United States Patent [19]

Mittleman

[11] 4,207,450

[45] Jun. 10, 1980

[54] CONTINUOUS OIL CONCENTRATION MONITOR

[75] Inventor: John Mittleman, Panama City, Fla.

[73] Assignee: The United States of America as represented by the Secretary of the Navy, Washington, D.C.

[21] Appl. No.: 915,496

[22] Filed: Jun. 14, 1978

[51] Int. Cl.² .................... G01N 21/26; G01N 21/34; G01N 33/18

[52] U.S. Cl. .................... 250/343; 23/230 HC; 23/230 M; 250/301; 422/62; 422/81

[58] Field of Search ............ 422/62, 68, 69, 81; 23/230 M, 230 HC; 250/301, 343

[56] References Cited

U.S. PATENT DOCUMENTS

| | | | |
|---|---|---|---|
| 2,430,895 | 11/1947 | Tuve et al. | 422/68 |
| 3,436,188 | 4/1969 | Boyd et al. | 422/81 X |
| 3,574,553 | 4/1971 | Weitz et al. | 422/81 X |
| 3,718,435 | 2/1973 | Tower | 422/81 |
| 4,045,671 | 8/1977 | Dille et al. | 250/301 X |
| 4,057,721 | 11/1977 | de Vial et al. | 250/301 |
| 4,103,162 | 7/1978 | Iwamoto et al. | 250/301 X |

FOREIGN PATENT DOCUMENTS 162354  4/1964  U.S.S.R. .................... 23/230 M

*Primary Examiner*—Joseph Scovronek
*Attorney, Agent, or Firm*—Richard S. Sciascia; Harvey A. David

[57] ABSTRACT

Apparatus for continuously monitoring the concentration of oil in a stream of water meters carbon tetrachloride through a first infrared analyzer to generate a reference signal, mixes the carbon tetrachloride with a sample stream of oily water to extract the oil, then separates and passes the oil containing carbon tetrachloride through a second infrared analyzer that is zeroed by the reference signal. The sample water stream is returned to the main flow and the carbon tetrachloride is reclaimed and recycled.

4 Claims, 3 Drawing Figures

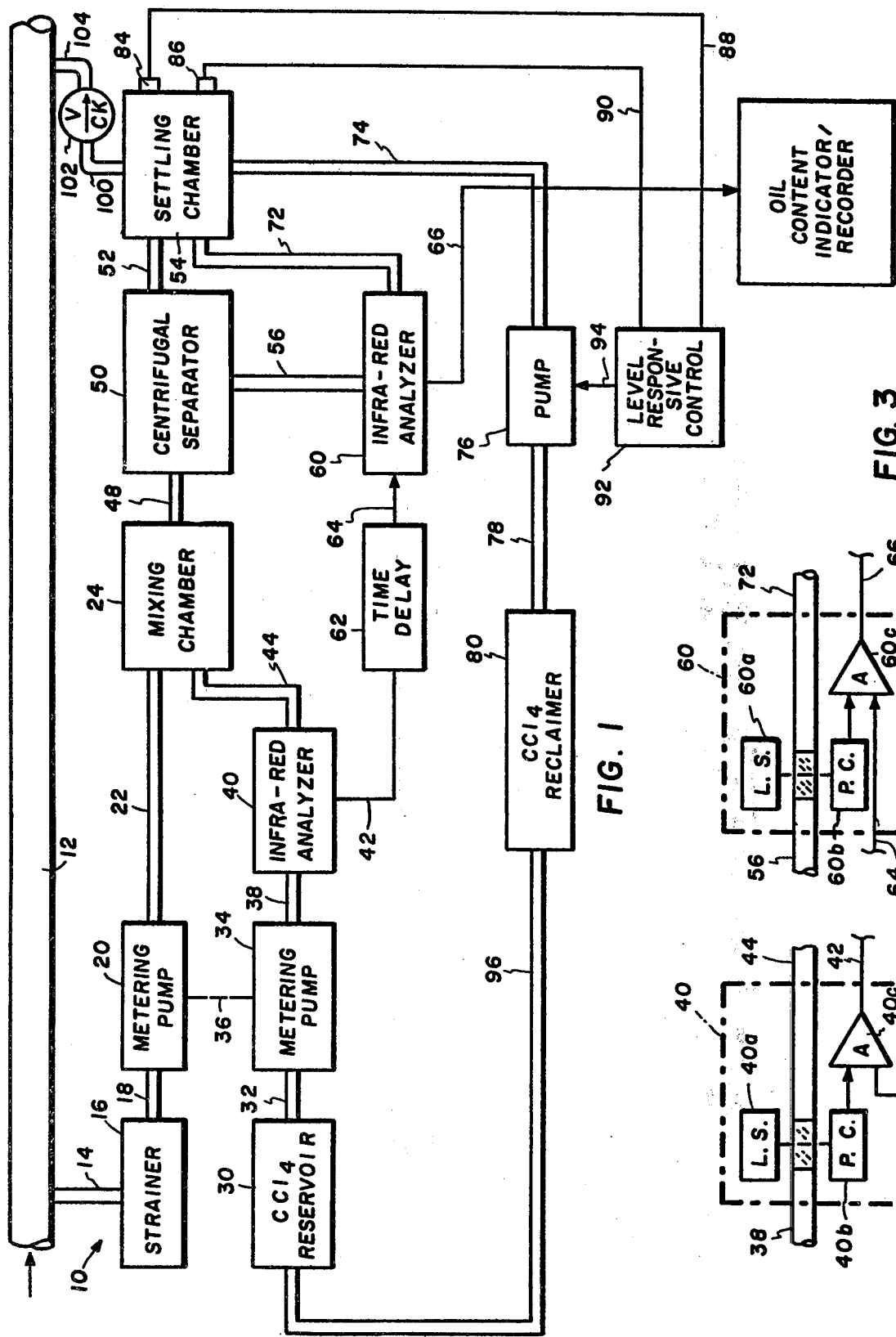
FIG. 1
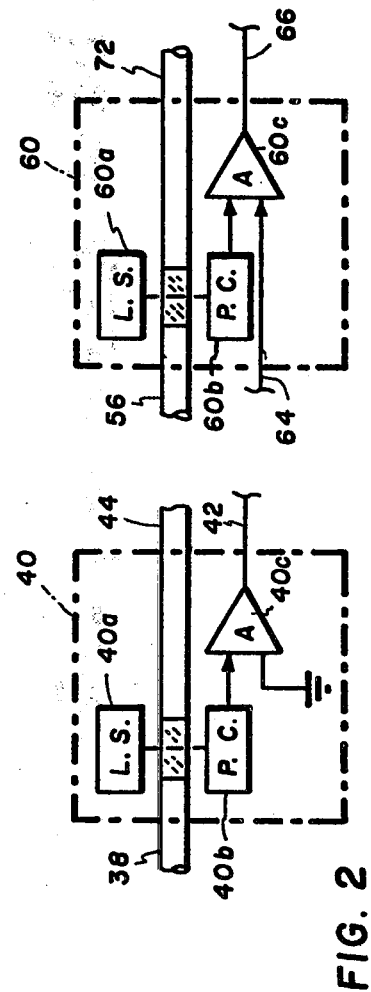
FIG. 3
FIG. 2

CONTINUOUS OIL CONCENTRATION MONITOR

BACKGROUND OF THE INVENTION

This invention relates to the determination of the amount of oil in water flowing in a conduit, and more particularly to an apparatus for continuously monitoring such oil content.

Many techniques are currently in use for determining the content of oil in water. Among these are a variety of procedures including measurements of fluorescence, turbidity, conductivity, and the like. One of the known techniques has been to utilize carbon tetrachloride to extract the oil from a discrete sample of oil containing water, and then to subject the carbon tetrachloride to infrared analysis to determine the amount of oil extracted from the sample. That technique, however, because of its use of discrete samples, is considerably time consuming and provides only an intermittent view of the amount of oil contained in a flow of water.

Because of the present day interest in avoiding contamination of the earth's waters with oil, it has become increasingly important to be able to monitor a flow of water for oil content on a continuous flow basis so as to provide a greater assurance of accuracy, and to permit rapid automated responses to changes in the oil content, for example, actuation of diverter means to prevent discharge to the environment of water containing more than a permissible low level of oil content.

Automated, general purpose discrete sample analyzing apparatus have been devised in an effort to increase the speed of analysis of discrete samples and approximate continuous flow monitoring of the type with which this invention is concerned. One example is provided in U.S. Pat. No. 4,013,413 to K. K. Stewart, et al. Such apparatus requires relatively complex valving, sample taking probe actuation, and the like, making truly repeatable readings unlikely over any substantial period of time. Moreover, that apparatus does not provide for automatic referencing of the analyzer element, an important feature which is included in the continuous oil concentration monitor embodying this invention.

SUMMARY OF THE INVENTION

With the foregoing in mind, it is a principal object of this invention to provide an improved apparatus for determining the content of oil in water.

Another, and important, object of this invention is the provision of an oil concentration monitoring apparatus that is capable of operating on a continuous flow of water containing oil so as to avoid the discontinuities and inaccuracies in data that are characteristic of discrete sample techniques of the prior art.

As another object, the invention aims to provide a continuous oil concentration monitoring apparatus including an infrared analyzer that is automatically continuously provided with a reference, whereby accuracy is maintained throughout continuous testing of long duration.

Yet another object is the provision of an apparatus of the foregoing character wherein the oil laden water or emulsion is divided into a main flow stream and a test or monitor flow stream, and wherein the oil is effectively removed from the test stream and the remaining substantially oil-free water is returned to the main flow stream.

Still another object is the provision of a continuously operable oil concentration monitor using an extracting agent or solvent such as carbon tetrachloride or one of the freon family to extract oil from the test flow stream for analysis in an infrared analyzer, and comprising means for removing the extracted oil from the solvent, whereby that solvent can be used in a continuous cycle oil concentration monitoring.

Other objects and many of the attendant advantages will be readily appreciated as the subject invention becomes better understood by reference to the following detailed description, when considered in conjunction with the accompanying drawings.

DESCRIPTION OF THE DRAWING

FIG. 1 is a schematic illustration, in block form, of a continuous oil concentration monitoring apparatus embodying the invention.

FIG. 2 is a diagrammatic illustration of a first infrared analyzer of the apparatus of FIG. 1; and FIG. 3 is a diagrammatic illustration of a second infrared analyzer of the apparatus of FIG. 1.

DESCRIPTION OF THE PREFERRED EMBODIMENT

Referring to FIG. 1, a continuous oil concentration monitoring apparatus is indicated generally at 10 and is shown in association with a conduit 12 carrying a primary flow of oily water, of which the concentration of oil is sought to be monitored on a continuous basis. Leading from the main flow conduit 12 is a sample flow conduit 14 connected to the inlet of a trash filter or strainer 16. The purpose of strainer 16 is to protect following positive displacement pump means and may be fairly coarse, that is, capable of removing particles of say 100 micron, or more.

The output of the strainer 16 is connected by a conduit 18 to the intake of a first positive displacement metering pump 20. The output of the pump 20 is connected, as shown by conduit 22 to one inlet of a mixing chamber 24.

A carbon tetrachloride reservoir 30 is connected by a conduit 32 to supply carbon tetrachloride to the intake of a second positive displacement metering pump 34. The pump 34 is mechanically connected to the pump 20, as shown by the dashed line 36, so as to deliver carbon tetrachloride in a predetermined ratio to the delivery of oily water by the pump 20. The pumps 20, 34 may be conventional positive displacement pumps such as peristaltic, gear, or the like, and are conveniently electrically driven.

The outlet of the pump 34 is connected via a conduit 38 to a first continuous flow infrared analyzer 40, which may comprise any of a number of commercially available infrared analyzers. Suffice it to say, with reference to FIG. 2, that light from an infrared source 40a is passed through the flow stream to an infrared sensitive photoelectric cell 40b. The cell responds to changes in the transmittance of infrared by the flow stream, which changes correspond to differences in purity of the passing carbon tetrachloride. The output of the cell is suitably amplified by an amplifier 40c and provided as an electrical reference signal represented by flow line 42. The purpose of this signal will be later made apparent.

Carbon tetrachloride that has passed through the analyzer 40 is carried by a conduit 44 to a second inlet of the mixing chamber 44. The mixing chamber 44 may be of any well known construction, such as a grid or baffle construction that promotes turbulence and rapid expansion, that will to a large extent preserve the general flow direction while encouraging complete transverse mixing of the carbon tetrachloride with the oily water. Any oil will be taken up by the carbon tetrachloride.

The single outlet of the mixing chamber 24 is connected by a conduit 48 to a centrifugal separator 50. The separator 50, which may be of conventional construction for separating heavier and lighter liquid components of a mixture on a continuous flow basis, serves to separate water as the lighter component from the carbon tetrachloride and oil solution as the heavier component. The separated water is fed from the centrifugal separator via a conduit 52 to a settling chamber 54.

The heavier, oil containing carbon tetrachloride is passed, via a conduit 56, from the separator 50 to a second infrared analyzer 60 for determination of the oil content of the carbon tetrachloride and oil solution. The analyzer 60 is similar to the first mentioned infrared analyzer 40. The amplifier of the analyzer 60, however, utilizes the electrical output of the analyzer 40 as a reference so that variations in oil content or other impurities affecting the infrared transmittance by the carbon tetrachloride that is mixed with the sample stream of water in chamber 24, will be effectively cancelled from the electrical output of the analyzer 60.

A finite time is required for the carbon tetrachloride to pass from the analyzer 40, through the mixing chamber 24, and the separator 50. In accordance with the preferred embodiment being described, the output signal of the first analyzer 40 on line 42 is applied to a time delay device 62 which provides a correspondingly time delayed reference signal as shown by line 64. Referring to FIG. 3, the analyzer 60 is shown to comprise an infrared light source 60a, a photo-cell 60b and an amplifier 60c. The delayed reference signal on line 64 is used to establish a zero reference level for the amplifier 60c of the second analyzer 60, the output of which is an electrical voltage signal, line 66, representative of the oil content of the main stream in conduit 12. This output signal is applied to a utilization device such as an oil content indicator/recorder 70 that provides a continuous record and/or display of the oil content of the main stream.

The oil containing carbon tetrachloride that is passed through the second analyzer 60 is directed, as shown by conduit 72, to the previously mentioned settling chamber 54, where it accumulates, along with any small amount of carbon tetrachloride that may have been carried from the centrifugal separator 50 by the water component directed by conduit 52 to that settling chamber.

The settling chamber 54 is provided with a carbon tetrachloride outlet conduit 74 that is connected to the inlet of a pump 76, the outlet of which is connected by conduit 78 to the inlet of a carbon tetrachloride reclaimer 80.

The settling chamber 54 is further provided with level sensing elements 84, 86, conveniently of the conductivity responsive type, for use in maintaining the carbon tetrachloride between predetermined upper and lower limits. Thus, the elements 84, 86 are electrically connected, as shown by lines 88, 90 to a level responsive pump control 92. The control 92 is electrically connected, as shown by line 94, to the pump 76 and is operative to actuate that pump when the carbon tetrachloride in chamber 54 reaches the level of sensing element 84, and to deactivate it when the carbon tetrachloride level is reduced to that of the sensing element 86.

The reclaimer 80 conveniently comprises an activated charcoal bed that removes oil from the carbon tetrachloride which is returned via a conduit 96 to the reservoir 30.

The upper portion of the settling chamber 54 is provided with an outlet conduit 100, a check valve 102, and a conduit 104 to the main flow conduit 12. Water accumulating over the carbon tetrachloride in the chamber 54 is driven by the force of the metering pumps 20, 34 into the primary flow conduit 12.

It will be recognized, of course, that other utilization means than the indicator/recorder 70 may be used with the invention. For example, the apparatus may be used to control a diverter valve in conduit 12 that will divert the flow of oily water to a suitable storage location should the oil content rise above some predetermined value as detected by the second analyzer 60. It will also be recognized that other solvents than carbon tetrachloride can be used, in the interest primarily of avoidance of the well known hararls of that substance to a person's health. Accordingly, it will be understood that the invention contemplates the substitution of other extracting agents or solvents having an affinity for oil and separable in the manners described from water. Among such substitute solvents are those known as freons.

Obviously, other embodiments and modifications of the subject invention will readily come to the mind of one skilled in the art having the benefit of the teachings presented in the foregoing description and the drawing. It is, therefore, to be understood that this invention is not to be limited thereto and that said modifications and embodiments are intended to be included within the scope of the appended claims.

What is claimed is:

1. Apparatus for continuously monitoring the concentration of oil in a main flow stream principally of water, said apparatus comprising:

first metering means for establishing a sample flow stream having a first colume flow rate;

a reservoir of a solvent capable of extracting said oil from said water;

second metering means for establishing a solvent flow stream from said reservoir at a second volume flow rate in a predetermined ratio to said first volume flow rate;

a first infrared analyzer connected in said solvent flow stream immediately downstream of said second metering means and operative to provide a continuously variable first electrical output signal that is continuously representative of changes in the infrared transmittance of said solvent in said solvent flow stream;

mixer means immediately downstream of said first infrared analyzer, for mixing said solvent flow stream with said sample flow stream whereby oil in said sample stream enters into solution with said solvent in an output flow of said mixer means;

centrifugal separator means, operable on said output flow of said mixer means, for providing a first output flow of said separator means comprised principally of water and a second output flow comprised principally of said solvent and any oil in solution therewith;

a second infrared analyzer connected in said second output flow of said centrifugal separator means;

time delay means, responsive to said first electrical output signal of said first analyzer, for providing a time delay in said first electrical output signal substantially equal to the time required for said solvent to flow from said first analyzer through said mixer means and through said centrifugal separator to said second analyzer;

said second analyzer being responsive to said first electrical output signal after said time delay and to the content of oil in said second output flow of said centrifugal separator means to provide a second electrical output signal that is continuously representative of changes in the concentration of oil in said main flow stream.

2. Apparatus as defined in claim 1, and wherein:

said first and second infrared analyzers each comprise photocell means and amplifier means, said amplifier means of said second analyzer comprising a differential amplifier.

3. Apparatus as defined in claim 2, and further comprising:

settling tank means, connected to collect said first output of said centrifugal separator and said second output of said centrifugal separator following flow thereof through said second analyzer, for separating water from said oil containing solvent for return of said water to said main flow stream; and reclaimer means, between said settling tank means and said reservoir, for removing oil from said solvent for return of said solvent to said reservoir.

4. Apparatus as defined in claim 3, and further comprising:

pump means for pumping said solvent from said settling tank means through said reclaimer means; and level responsive control means for energizing said pump means when said solvent rises to a first predetermined level in said settling tank means and for deenergizing said pump means when said solvent falls to a second predetermined level.

* * * * *